(12) United States Patent
Kurz et al.

US006491930B2

(10) Patent No.: US 6,491,930 B2
(45) Date of Patent: Dec. 10, 2002

(54) STABLE COSMETIC FORMULATION CONTAINING BUTYLMETHOXYDIBENZOYLMETHANE

(75) Inventors: Thekla Kurz, Stefan-George-Weg (DE); HansJürgen Driller, Krötenmgasse (DE); Sabine Hitzel, Langgasse (DE); Dorothee Wille, In den Wingerten (DE)

(73) Assignee: Merck Patent Gesellschaft MIT, Darmstadt (DE)

( * ) Notice: Subject to any disclaimer, the term of this patent is extended or adjusted under 35 U.S.C. 154(b) by 0 days.

(21) Appl. No.: 09/530,733

(22) PCT Filed: Oct. 31, 1998

(86) PCT No.: PCT/EP98/06901

§ 371 (c)(1),
(2), (4) Date: May 5, 2000

(87) PCT Pub. No.: WO99/24006

PCT Pub. Date: May 20, 1999

(65) Prior Publication Data

US 2002/0150599 A1 Oct. 17, 2002

(30) Foreign Application Priority Data

Nov. 12, 1999 (DE) ......................................... 197 50 029

(51) Int. Cl.[7] ................................................ A61K 7/00

(52) U.S. Cl. .......................... 424/401; 424/59; 514/688; 514/694

(58) Field of Search ................... 424/401, 59; 514/688, 514/694

(56) References Cited

U.S. PATENT DOCUMENTS 5,292,529 A * 3/1994 Gregory et al. ............... 424/59

FOREIGN PATENT DOCUMENTS

| WO | 9217159 | 10/1992 |
|----|---------|---------|
| WO | 9421221 | 9/1994 |
| WO | 9747280 | 12/1997 |
| WO | 9813016 | 4/1998 |

OTHER PUBLICATIONS

Derwent WPI abstract of JP 08 208403.

* cited by examiner

*Primary Examiner*—Michael G. Hartley
*Assistant Examiner*—Michael A. Williamson
(74) *Attorney, Agent, or Firm*—Millen, White, Zelano & Branigan, P.C.

(57) ABSTRACT

The invention relates e.g. to the use of aldehydes and/or ketones for improving the stability of cosmetic formulations containing butylmethoxydibenzoylmethane as organic light protection filters in conjunction with inorganic light protection filters.

10 Claims, No Drawings

STABLE COSMETIC FORMULATION CONTAINING BUTYLMETHOXYDIBENZOYLMETHANE

The present invention relates, inter alia, to the use of aldehydes and/or ketones for improving the stability of cosmetic formulations which comprise, as organic light protection filter, butylmethoxydibenzoyl methane combined with inorganic light protection filters.

As is known, the skin is sensitive to solar rays, which can cause ordinary sunburn or an erythema, and also burns of greater or lesser severity.

However, solar rays also have other adverse effects: they cause the skin to lose its elasticity and form wrinkles and these lead to premature ageing. Dermatoses may also sometimes be observed. In the extreme case, some people develop skin cancer.

It is also desirable to protect hair against photochemical damage in order to prevent changes in shade, bleaching or damage of a mechanical nature.

As is known, the most dangerous solar rays are the ultraviolet rays having a wavelength of less than 400 nm. It is also known that as a result of the presence of the ozone layer in the Earth's atmosphere, which absorbs some solar radiation, the lower limit of the ultraviolet rays which reach the Earth's surface is approximately 280 nm.

The sunscreen filters customarily used in cosmetics nowadays are divided into UVA and UVB filters. For both UV ranges, there are many tried and tested substances known from the specialist literature, substances such as Eusolex® 6300 or Eusolex® 232, dibenzoylmethanes such as Eusolex® 9020 (butylmethoxybenzoylmethane as UVA filter) or Eusolex® 8020, benzophenones and also octyl triazones (Uvinul® T 150) being listed here merely by way of example.

However, the problem with many sunscreen preparations is that many light protection filters are sensitive substances and have low stability towards ultraviolet rays; they break down at a greater or lesser rate. This results in problems with regard to shelf life and effectiveness of the corresponding cosmetic formulations.

In sunscreen formulations organic light protection filters are also combined with inorganic filters such as titanium dioxide, zinc oxide or iron oxides. A frequently used organic light protection filter is butylmethoxydibenzoylmethane (BMDM). However, the effectiveness of butylmethoxydibenzoylmethane is significantly reduced in this combination with metal oxides as a result of the ability of the butylmethoxydibenzoylmethane, as diketone, to form complexes with a variety of metal ions. Such reactions are known with ions of titanium, zinc, iron and aluminium. However, the metal ions do not primarily have to be in the form of ions, but can also react in the form of oxides. These reactions are of course undesired in sunscreen formulations.

The object was therefore to find a way of preventing this undesired reaction and thereby achieving an improvement in the stability of cosmetic preparations which comprise butylmethoxydibenzoyl methane together with inorganic light protection filters.

Surprisingly, we have now found that the undesired complex formation can be prevented by active aldehydes and/or ketones present. Here, the aldehyde and/or keto groups bond to the active sites of the metal oxide particle surfaces and thus prevent the possibility of the BMDM contacting with the metal oxides.

The invention thus provides for the use of aldehydes and/or ketones for stabilizing cosmetic formulations which comprise butylmethoxydibenzoyl methane combined with inorganic light protection filters.

The invention also provides a cosmetic preparation comprising inorganic light protection filters and butylmethoxydibenzoylmethane, characterized in that aldehydes and/or ketones are added to improve the stability.

The invention further provides a process for improving the stability of cosmetic preparations comprising butylmethoxydibenzoylmethane combined with inorganic light protection filters, characterized in that aldehydes and/or ketones are added.

Suitable inorganic light protection filters are primarily titanium dioxide, zinc oxide or iron oxides, and also cerium oxide. In addition, it is also possible for these oxides to be aftercoated with other metal oxides, for example with aluminium oxide.

The content of these inorganic particles in the formulations according to the invention is 0.1 to 30% by weight, preferably 0.5 to 10% by weight.

The butylmethoxydibenzoylmethane is represented in the preparation according to the invention with a content of from 0.1 to 10% by weight, preferably from 0.5 to 3% by weight.

The BMDM can be present in the cosmetic formulations according to the invention on its own or else in combination with one or more UV filters from other classes of substance, each of which can be present in an amount of from 0.01 to 40% by weight, preferably from 0.1 to 10% by weight.

Suitable aldehydes or ketones are so-called active or activated compounds. Preference is given to using ketols, diketones or ketones or aldehydes which are in conjugation to a double bond, and also formaldehyde or formaldehyde-releasing substances.

By way of example, the following particularly preferred compounds may be mentioned: formaldehyde (also as formaldehyde-releasing preservative), dihydroxyacetone, vanillin, erythrulose, hydroxy acetone, sugars, such as sorbose, fructose or glucose.

The content of aldehydes and/or ketones is at least 100 ppm and at most 10% by weight.

It is also possible to use combinations of aldehydes and ketones. In this connection, 1:1 combinations are preferably suitable. For example, a combination of formaldehyde and vanillin or of formaldehyde and erythrulose.

A very particularly preferred formulation according to the invention comprises formaldehyde as aldehyde since this can, for the sake of simplicity, be used simultaneously as preservative.

The substance butylmethoxybenzoylmethane (Eusolex® 9020) is, as already mentioned, known and can be obtained commercially, e.g. from Merck KGaA, Darmstadt.

The aldehydes and ketones (or their precursors) can, on the one hand, be added directly to the cosmetic formulation, and on the other hand it is also possible to admix or to wash the metal oxides with an aldehyde or ketone as early as during their preparation, before they are added to the cosmetic formulation.

For the effect according to the invention, this is of no consequence.

The invention further provides a method of protecting the skin and/or natural or sensitized hair against solar rays, a cosmetic preparation according to the present invention being applied to the skin or the hair.

"Sensitized hair" means hair which has been subjected to a permanent wave treatment, or to a colouring or bleaching process.

If the cosmetic preparation according to the invention is used to protect the human epidermis from UV rays, it is in a variety of forms customarily used for this purpose. For example, it can, in particular, be in the form of oily, oily-aqueous, aqueous-alcoholic or oily-alcoholic lotions, emulsions, such as a cream or milk (W/O or O/W, where W=water and O=oil), in the form of oily-alcoholic, oily-aqueous or aqueous alcoholic gels or as solid sticks or powders, or can be formulated as a spray or aerosol.

The formulation according to the invention can comprise further cosmetic additives which are customarily used in this type of preparations, such as thickeners, emollients, moisturizers, surfactants, preservatives, antifoams, perfumes, waxes, lanolin, propellants, dyes and/or pigments which colour the composition itself or the skin, and other ingredients ordinarily used in cosmetics.

The solubilizing agent can be an oil, wax or other fatty substance, a lower monoalcohol or a lower polyol or mixtures thereof. Particularly preferred monoalcohols or polyols include ethanol, isopropanol, propylene glycol, glycerol and sorbitol.

A preferred embodiment of the invention is an emulsion which is in the form of a protective cream or milk and which, in addition to BMDM, optionally in combination with other organic light protection agents, the inorganic light protection filters and the amount of aldehydes and/or ketones according to the invention, comprises fatty alcohols, fatty acid esters, in particular triglycerides of fatty acids, fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such -as ethanol, or a glycol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener, such as diatomaceous earth. The oily-alcoholic gels further comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, use is normally made of the customary propellants, such as alkanes, fluoroalkanes and chlorofluoroalkanes.

If a formulation is formulated as a spray, use is normally made of aqueous-alcoholic solutions.

If the composition according to the invention is intended to protect natural or sensitized hair from UV rays, then it can be in the form of a shampoo, lotion, mousse, gel or emulsion for rinsing out, the respective formulation being applied before or after shampooing, before or after colouring or bleaching, or before or after permanent waving; or the composition is in form of a lotion, mousse or gel, for styling and treating, a lotion, mousse or gel for brushing or setting a water-wave, a hairspray, permanent wave composition, colorant or bleach for the hair. Apart from the compound according to the invention, this composition can comprise a variety of additives used in this type of composition, such as surfactants, thickeners, polymers, emollients, preservatives, foam stabilizers, electrolytes, organic solvents, silicone derivatives, oils, waxes, degreasing agents, dyes and/or pigments which colour the composition itself or the hair, or other ingredients customarily used for hair care.

The cosmetic preparations according to the invention can be prepared using techniques which are well known to the person skilled in the art.

The formulations according to the invention can also be used for the preventative treatment of inflammations and allergies of the skin and for preventing certain types of cancer.

It is assumed that a person skilled in the art is able to utilize the above description in the widest sense without further explanations. The preferred embodiments are therefore merely to be seen as a descriptive disclosure which is by no means limiting.

The examples below serve to illustrate the invention in more detail. However, they are not suitable for limiting the subject-matter of the invention to these examples on their own.

EXAMPLE 1

The following components are used to prepare a sunscreen cream (O/W) according to the invention.

|   |   |   | % by wt |
|---|---|---|---|
| A | Eusolex ® 9020 (Art. No. 105844) (Butylmethoxydibenzoylmethane) | (1) | 1.00 |
|   | Arlatone 983 S | (2) | 1.50 |
|   | Arlatone 985 | (2) | 2.20 |
|   | Brij 76 | (2) | 1.50 |
|   | Miglyol 812 (neutral oil) | (3) | 10.00 |
| B | Sorbitol F liquid (Art. No. 102993) | (1) | 2.50 |
|   | 1,2-propanediol (Art. No. 107478) | (1) | 2.50 |
|   | Preservatives | (1) | q.s. |
|   | Demin. water | | ad100.00 |
| C | Carbomer 934 | (4) | 0.50 |
| D | Tris (hydroxymethyl) aminomethane (Art. No. 108386) | (1) | 0.36 |
|   | Demin. water | | 9.64 |
| E | Eusolex ® T-2000 (Art. No. 105373) | (1) | 5.00 |
|   | Formaldehyde solution (Art. No. 159174) | (1) | 0.10 |

Preparation:

Phase E is mixed and carefully stirred and dried. Phase B is mixed, Carbomer 934 is added thereto, and the mixture is left to, swell until it is homogeneous. The premixed phase D is then added and the mixture is homogenized. Phase E is then added to this mixture, which is then heated to 80° C. Phase A is combined and heated to 75° C. With slow stirring, phase A is stirred into the phase prepared beforehand from B–E.

Preservatives:

0.05% of propyl 4-hydroxybenzoate (Art. No. 107427)

0.15% of methyl 4-hydroxybenzoate (Art. No. 106757)

Sources of supply:

(1) Merck KGBA, Darmstadt (2) ICI, Essen (3) Hüls Troisdorf AG, Witten (4) Goodrich, Neuss

EXAMPLE 2

The following components are used to prepare a sunscreen cream (O/W) according to the invention.

|   |   |   | % by wt |
|---|---|---|---|
| A | Eusolex ® 9020 (Art. No. 105844) (Butylmethoxydibenzoylmethane) | (1) | 1.00 |
|   | Eusolex ® T-2000 (Art. No. 105373) | (1) | 5.00 |
|   | Arlatone 983 S | (2) | 1.50 |
|   | Arlatone 985 | (2) | 2.20 |
|   | Brij 76 | (2) | 1.50 |
|   | Miglyol 812 (neutral oil) | (3) | 10.00 |

-continued

| | | | % by wt |
|---|---|---|---|
| B | Sorbitol F liquid (Art. No. 102993) | (1) | 2.50 |
| | 1,2-propanediol (Art. No. 107478) | (1) | 2.50. |
| | Formaldehyde solution (Art. No. 159174) | (1) | q.s. |
| | Demin. Water | | ad100.00 |
| C | Carbomer 934 | (4) | 0.50 |
| D | Tris (hydroxymethyl) aminomethane (Art. No. 108386) | (1) | 0.36 |
| | Demin. Water | | 9.64 |

Preparation:

Phase B is mixed, Carbomer 934 is added thereto, and the mixture is left to swell until it is homogeneous. The premixed phase D is then added and homogenized. The mixture is then heated to 80° C. Phase A is combined and heated to 75° C. With slow stirring, phase A is stirred into the phase prepared beforehand from B–D.

Sources of supply:

(1) Merck KGaA, Darmstadt
(2) ICI, Essen
(3) Hüls Troisdorf AG, Witten
(4) Goodrich, Neuss

What is claimed is:

1. A cosmetic formulation comprising at least one inorganic light protection filter and butylmethoxydibenzoylmethane, and at least one additional component which additional component improves the stability of the formulation, whereby the additional component is a combination of formaldehyde and vanillin or of formaldehyde and erythrulose.

2. A cosmetic formulation according to claim 1, whereby the at least one inorganic light protection filter present is a titanium dioxide, zinc oxide or iron oxide, optionally after-coated with other metal oxides.

3. A cosmetic formulation according to claim 1, whereby the content of butylmethoxydibenzoylmethane is 0.1 to 10% by weight.

4. A cosmetic formulation according to claim 1, whereby the content of the additional component is 100 ppm to 10% by weight.

5. A cosmetic formulation according to claim 1, whereby the content of at least one inorganic light protection filter is 0.1 to 30% by weight.

6. A cosmetic formulation comprising at least one inorganic light protection filter and butylmethoxydibenzoylmethane, and at least one additional component which additional component improves the stability of the formulation, whereby the additional component is formaldehyde.

7. A cosmetic formulation according to claim 6, whereby the at least one inorganic light protection filter present is a titanium dioxide, zinc oxide or iron oxide, optionally after-coated with other metal oxides.

8. A cosmetic formulation according to claim 6, whereby the content of butylmethoxydibenzoylmethane is 0.1 to 30% by weight.

9. A cosmetic formulation according to claim 6, whereby the content of the additional component is 100 ppm to 10% by weight.

10. A cosmetic formulation according to claim 6, whereby the content of at least one inorganic light protection filter is 0.1 to 30% by weight.

* * * * *

UNITED STATES PATENT AND TRADEMARK OFFICE
CERTIFICATE OF CORRECTION

PATENT NO.   : 6,491,930 B2
DATED        : December 10, 2002
INVENTOR(S)  : Kurz et al.

It is certified that error appears in the above-identified patent and that said Letters Patent is hereby corrected as shown below:

Column 6,
Line 29, change "30%" to -- 10% --.

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,491,930 B2  Page 1 of 1
DATED : December 10, 2002
INVENTOR(S) : Kurz et al.

It is certified that error appears in the above-identified patent and that said Letters Patent is hereby corrected as shown below:

Column 6,
Line 26, change "30%" to -- 10% --.

This certificate supersedes Certificate of Correction issued December 2, 2003.

Signed and Sealed this

Twenty-second Day of March, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,491,930 B2 |
| APPLICATION NO. | : 09/530733 |
| DATED | : December 10, 2002 |
| INVENTOR(S) | : Thekla Kurz et al. |

It is certified that error appears in the above-identified patent and that said Letters Patent is hereby corrected as shown below:

<u>Title Page</u>

Item (73) Assignee is to be changed to read --Merck Patent Gesellschaft MIT Beschrfankter Haftung, Darmstadt, Fed Rep Germany--.

Signed and Sealed this

Second Day of October, 2007

JON W. DUDAS
*Director of the United States Patent and Trademark Office*